US009119769B2

(12) United States Patent
Atwood et al.

(10) Patent No.: US 9,119,769 B2
(45) Date of Patent: Sep. 1, 2015

(54) METHOD FOR TRANSFORMING PHARMACEUTICAL CRYSTAL FORMS

(71) Applicant: The Curators of the University of Missouri, Columbia, MO (US)

(72) Inventors: Jerry Lee Atwood, Columbia, MO (US); Jian Tian, Richland, WA (US); Scott John Dagarno, Edinburgh (GB)

(73) Assignee: The Curators of the University of Missouri, Columbia, MO (US)

( * ) Notice: Subject to any disclaimer, the term of this patent is extended or adjusted under 35 U.S.C. 154(b) by 129 days.

(21) Appl. No.: 13/722,547

(22) Filed: Dec. 20, 2012

(65) Prior Publication Data

US 2013/0274457 A1    Oct. 17, 2013

Related U.S. Application Data

(60) Provisional application No. 61/631,253, filed on Dec. 30, 2012.

(51) Int. Cl.
*C07H 17/08* (2006.01)
*A61J 3/00* (2006.01)
*C07D 401/12* (2006.01)

(52) U.S. Cl.
CPC *A61J 3/00* (2013.01); *C07D 401/12* (2013.01)

(58) Field of Classification Search
None
See application file for complete search history.

(56) References Cited

U.S. PATENT DOCUMENTS

| 5,578,732 | A | 11/1996 | Kato |
| 5,844,105 | A | 12/1998 | Liu |
| 5,858,986 | A | 1/1999 | Liu |
| 5,945,405 | A | 8/1999 | Spanton |
| 6,002,011 | A | 12/1999 | Kato |
| 6,396,624 | B1 | 5/2002 | Nissov |
| 6,599,884 | B2 | 7/2003 | Avrutov |
| 6,627,743 | B1 | 9/2003 | Liu |
| 2009/0264438 | A1 * | 10/2009 | Jegorov et al. .......... 514/252.18 |

FOREIGN PATENT DOCUMENTS

WO    WO 2005061524 A2 *  7/2005

OTHER PUBLICATIONS

Braun, Crystal Growth & Design, 2011, vol. 11, 210-220.*
Boldyreva, Polymorphism of glycine. Thermodynamic and structural aspects, 2004.*
Landers, J. Phys. Chem. 1980, 84, 3573-3577.*
Tian et al. Chem. Commun., 2011, 47, 701-703.*
Tian et al. Journal of the American Chemical Society 2011, 133, 1399-1404.*
Bernstein, J.; Dunitz, J.D.; Disappearing Polymorphs; Acc. Chem. Res.; 1995, 28, 193-200.
Bettini, R.; Bonassi, L.; Castoro, V.; Rossi, A. Zema, L.; Gazzaniga, A.; Giordano. F.; Solubility and Conversion of Carbamazepine Polymorphs in Supercritical Carbon Dioxide; Eur, J. Pharm. Sci.; 2001, 13, 281-286.
Brittain, H.G.; Effects of Mechanical Processing on Phase Composition; J. Pharm. Sci.; 2002, vol. 91, No. 7, 1573-1580.
Davey, R.J.; Pizzas, Polymorphs and Pills; Chem. Comm. (The Royal Society of Chemistry); 2003, 1463-1467.
Dawson, A.; Allan, D.R.; Belmonte, S.A.; Clark, S.J.: David, W.F.; McGregor, P.A.; Parsons, S.; Pulham, C.R.; Sawyer, L.; Effect of High Pressure on the Crystal Structures of Polymorphs of Glycine; Cryst. Growth & Des.; 2005, vol. 5, No. 4, 1415-1427.
Fabbiani. F.P.A.; Pulham, C.R.; High-Pressure Studies of Pharmaceutical Compounds and Energetic Materials; Chem. Soc. Rev.; 2006, 35, 932-942.
Iwasaki, H.; Sugawara, Y.; Adachi, T.; Morimoto, S.; Watanabe, Y.; Structure of 6-O-Methylerythromycin A (Clarithromycin); Acta Cryst.; 1993, C49, 1227-1230.
Jin, Z.M.; Ma, L.L.; Wei, W.X.; Lin, C.S.; Li, W.Z.; Molecular and Crystal Structure of an Ethanol Solvate of 6-O- Methylerythromycin A; J. Struct. Chem.; 2009, vol. 50, No. 1, 185-189.
Johnstone, R.D.L.; Ieva, M.; Lennie, A.R.; McNab, H.; Pidcock, E.; Warren, J.E.; Parsons, S.; Pressure As a Tool in Crystal Engineering: Inducing a Phase Transition in a High-Z' Structure; ChrystEngComm, 2010, 12, 2520-2523.
Liang, J-H; Yao, G.W.; A New Crystal Structure of Clarithromycin; J. Chem. Crystallogr.; 2008, 38:61-64.
Moribe, K.; Tozuka, Y.; Yamamoto, K.; Supercritical Carbon Dioxide Processing of Active Pharmaceutical Ingredients for Polymorphic Control and for Complex Formation; Adv. Drug Delivery Rev.; 2008, 60, 328-338.
Morimoto, S.; Misawa, Y.; Adachi, T.; Nagate, T.; Watanabe, Y.; Omura, S.Y.; Chemical Modification of Erythromycins; J. Antibiotics, 1990, vol. 43, No. 3, 286-294.
Stephenson, G.A.; Stowell, J.G.; Toma, P.H.; Pfeiffer, R.R.; Byrn, S.R.; Solid-State Investigations of Erythromycin A Dihydrate: Structure, NMR Spectroscopy, and Hygroscopicity; J. Pharm. Sci.; 1997, vol. 86, No. 11, 1239-1244.
Subramanian. B.; Rajewski, R.O.; Snavely, K.; Pharmaceutical Processing with Supercritical Carbon Dioxide; J. Pharm. Sci.; 1997, vol. 86, No. 8, 885-890.
Thallapally, P.K.; McGrail, B.P.; Dalgarno, S.J.; Schaef, H.T.; Tian, J.; Atwood, J.L.; Gas-Induced Transformation and Expansion of a Non-Porous Organic Solid; Nature Materials, 2008, vol. 7, 146-150.
Tian, J.; Thallapally, P.K.; Dalgarno, S.J.; Atwood, J.L.; Free Transport of Water and CO2 in Nonporous Hydrophobic Clarithromycin Form II Crystals; J. Am. Chem. Soc.; 2009, 131, 13216-13217.
Tozuka, Y.; Kawada, D.; Oguchi, T.; Yamamoto, K.; Supercritical Carbon Dioxide Treatment As a Method for Polymorph Preparation of Deoxycholic Acid; Int. J. Pharm.; 2003, 263, 45-50.
Vyas, K.; Sivalakshmidevi, A.; Om Reddy, G.; Lansoprazole, an Antiulcerative Drug; Acta Crystallographica Section C, 2000, C56, e572-573.

* cited by examiner

*Primary Examiner* — Layla Bland
(74) *Attorney, Agent, or Firm* — Polsinelli PC

(57) ABSTRACT

The present invention provides gas-induced method for phase-transforming organic solids, such as pharmaceutical crystals. The inventive method subjects the polymorphs of pharmaceutical agents to various pressures of gases (such as $CO_2$, $N_2O$, and $CH_4$) to induce phase transform with ease.

9 Claims, 5 Drawing Sheets

A)  B)

METHOD FOR TRANSFORMING PHARMACEUTICAL CRYSTAL FORMS

This application claims the benefit of priority of U.S. Provisional Application No. 61/631,253, filed Dec. 30, 2011, the disclosure of which is hereby incorporated by reference as if written herein in its entirety.

The present invention relates to method for transforming among different polymorphic forms of organic solids, more specifically, to a gas-induced transformation method of pharmaceutical crystals.

The phenomenon of polymorphism, the ability of a compound to crystallize into more than one distinct crystal species, is a major factor in the pharmaceutical industry, as different polymorphs can display markedly disparate stabilities, solubility, and/or bioavailability. Different physical forms can be classified as polymorphs or pseudopolymorphs (solvates and hydrates). Polymorphs have the same chemical composition but different crystal structures. Pseudopolymorphs are crystalline adducts that contain solvent molecules (water in the case of hydrates) within the crystal structure, either in stoichiometric or non-stoichiometric proportions. Sometimes a drug product can be in a desolvated solvate, formed when solvent is removed while the crystal structure is essentially retained. The different crystal structures, adopted by a given compound under different crystallization conditions, have a strong effect on the properties of the substances. In fact, for a given material, thermodynamic, kinetic, packing, spectroscopic, surface and mechanical properties are different for different physical forms. The difference in the physico-chemical properties can significantly impact the manufacturing process as well as the in vivo performance of the final drug product. It should also be considered that a variety of unintentional conversion of polymorphs, desolvation of solvates, and solvates formation can occur during the pharmaceutical processes of granulation, drying, spray-drying, lyophilization, compression, etc. Further, some materials can only be desolvated through techniques that are difficult to apply on an industrial scale.

In addition, many compounds can exist as amorphous forms, characterized by the absence of long-range molecular order. From a thermodynamic point of view, the amorphous forms have a higher energy content than the crystalline state, leading to lower stability and higher reactivity. The lower physical stability also implies higher solubility and dissolution rates that are generally desirable characteristics for pharmaceutical compounds. For example, in the case of novobiocin, the crystalline form is poorly absorbed and does not provide therapeutically adequate plasma levels upon oral administration. The amorphous phase is readily absorbed and is therapeutically active. This difference in bioavailability is related to the different solubilities between the two forms in water.

Sometimes, especially after processing operations, a solid of low crystallinity intermediate between that of pure crystalline solids and an amorphous solid can be formed.

Modern drug delivery systems require control of the physicochemical properties of particles including their size, shape, surface properties, and crystalline purity. The reproducible preparation of organic crystals in a specifically tailored form and size is a major issue that must be addressed by chemists, engineers, and pharmaceutical formulators. These specific characteristics are important factors to control technological and biopharmaceutical properties of drug products, particularly in the case of inhalation and intravenous dosage forms that require precise control of the particle size, shape, density, and surface properties.

The regulatory authorities also emphasize the importance of solid-state and crystallographic purity in addition to careful monitoring of the polymorphism of drugs and excipients. In this regard, the guideline Q6A of the international conference on harmonization underlines the importance of characterizing crystallinity and polymorphism. Likewise, the FDA requires information about the relationship between structure and stability, as well as complete structural proof on crystalline drugs, preferably derived from a single crystal.

Like other physical characteristics, the solid-state of a drug product deeply influences all steps of the development of pharmaceuticals, from discovery to successful marketing. Pharmaceutical companies quite often must face unexpected and undesired productive and/or clinical problems due to the appearance of crystal forms different from that used for drug product development. A paramount example in this regard is the Ritonavir (Norvir®, Abbott) case that dramatically underscored the need for extensive preliminary drug solid-state characterization. The discovery of new polymorphic forms is also very relevant in the context of patent protections and, as a consequence, has significant economic implications.

Pharmaceutical crystals represent one of the most important classes of organic solids due to their inherent importance to human health. Numerous efforts have currently been devoted to polymorph control of drug substances during the preformulation stage to meet technological and biopharmaceutical requirements. The traditional processes used to obtain different polymorphs are extreme pressure (generally 1000 to 100,000 bar) compression, crushing/milling, air micronization, sublimation, evaporation, vapor diffusion, thermal treatment and recrystallization from solvents or melts. A relatively recent approach for obtaining pharmaceutical materials in pure physical forms is represented by technologies based on supercritical fluids (SCF). By proper adjustment of the operating conditions as well as physical and chemical parameters (pressure, temperature, drug concentration, flow and nature of supercritical fluid and organic solvent), materials of a desired crystal form can be generated.

There are countless examples of biologically active compounds that have proven to be difficult to control in the solid state, wherein the polymorph formed during the industrial process may be not be the polymorph desired for the dosage form.

One such example, Clarithromycin (1, 6-O-methylerythromycin A, FIG. 1A) is a semisynthetic macrolide antibiotic that has been widely studied in this regard and that exhibits excellent activity against various bacteria. It has been shown (through numerous synthetic routes, including various methods of crystallization) that Clarithromycin 1 can exist in five different crystalline forms designated 0, I, II, III, and IV (although III and IV have not been commercialized). Form 0 crystals exist as a solvate form and both form I and form II crystals are anhydrous. Clarithromycin is currently marketed in the United States under the trademark Biaxin, and is formulated using form II. A key step in the process of isolation of form II involves heating form I at ~110-115° C. overnight (~18 h). FIG. 2 illustrates a known phase transformation scheme of Clarithromycin.

Another example is Lansoprazole (2, FIG. 1B), which is a proton pump inhibitor (PPI) that is currently the No. 8 best-selling drug in the United States market under the trademark Prevacid. Commercially important crystal forms of Lansoprazole 2 include a solvate form (1:1 ethanol hydrate) and a solvent-free form. The stable solvent-free marketing agent is currently isolated by stirring the 1:1 ethanol hydrate of 2 (that is prone to decomposition) in water, followed by filtration and intensive drying to remove surface water, which is difficult for industry scale process.

Therefore, there is a need to provide a new and improved method to control and facilitate the transformations among different polymorphic forms of organic solids, especially pharmaceutical crystals.

SUMMARY OF INVENTION

The invention provides a new and improved method for controlling phase transitions among the polymorphic forms of an organic solid. The inventive method employs simple pressurization of gas (such as $CO_2$) to induce transformations among different polymorphic forms of an organic solid with ease. More specifically, the method of transforming an organic solid from a first polymorphic form to a second polymorphic form comprises the step of subjecting said organic solid to a pressurized gas under low to moderate pressure at room temperature to a mildly elevated temperature for a period of time. According to one embodiment of the invention, the pressurized gas may be $CO_2$, $N_2O$, or $CH_4$, and the pressure may be 1 atm and up, whereas when the pressure is elevated, the temperature may be lowered with shortened durations.

This is in contrast to techniques using SCF, wherein a solid is dissolved in a super-critical fluid (gas), and then the solid is precipitated by reducing the pressure of the gas, causing the solid to crash out of solution.

Disclosed herein is a method for transforming an organic solid from a first polymorphic form to a second polymorphic form comprising the step of subjecting said organic solid to a pressurized gas at less than 40 atm, at a temperature under 150° C. for a period of time, wherein said combination of pressure and temperature is sufficient to cause a polymorphic transformation in said organic solid.

Disclosed herein is a method for transforming an organic solid from a mixture of polymorphic forms to a single polymorphic form comprising the step of subjecting said organic solid to a pressurized gas at less than 40 atm, at a temperature under 150° C. for a period of time, wherein said combination of pressure and temperature is sufficient to cause a polymorphic transformation in said organic solid.

Disclosed herein is a method for transforming an organic solid from a solvated form to a desolvated form comprising the step of subjecting said organic solid to a pressurized gas at less than 40 atm, at a temperature under 150° C. for a period of time, wherein said combination of pressure and temperature is sufficient to cause desolvation in said organic solid.

Disclosed herein is a method of screening an organic solvent for polymorphic form comprising the step of subjecting said organic solid to a pressurized gas at less than 40 atm, at a temperature under 150° C. for a period of time, wherein said combination of pressure and temperature is sufficient to cause a polymorphic transformation in said organic solid.

In an embodiment, said pressurized gas is chosen from $CO_2$, $N_2O$, $CH_4$, $H_2$, He, $N_2$, $O_2$, and air.

In an embodiment, said pressurized gas is chosen from $CO_2$, $N_2O$, and $CH_4$.

In an embodiment, said organic solid is subjected to a pressurized gas at less than 10 atm.

In an embodiment, said organic solid is subjected to a pressurized gas at less than 5 atm.

In an embodiment, said organic solid is subjected to temperature under 100° C.

In an embodiment, said organic solid is subjected to temperature under 50° C.

In an embodiment, said organic solid is chosen from an antibiotic and a proton pump inhibitor.

In an embodiment, said organic solid is chosen from clarithromycin and lansoprazole.

In an embodiment, said period of time lasts less than 72 hours.

In an embodiment, said period of time lasts less than 24 hours.

DETAILED DESCRIPTION OF INVENTION

Unless otherwise defined, all technical and scientific terms used herein have the same meaning as commonly understood by one of ordinary skill in the art to which this invention belongs. All publications, patent application, patents, and other references mentioned herein are incorporated by reference in their entirety.

The invention teaches that simple pressurization of polymorphic forms of an organic solid, such as a pharmaceutical agent, can effect phase transitions among the forms with ease. More specifically, the inventive method comprises the step of subjecting an organic solid to a pressurized gas under low to moderate pressure at room temperature to a mildly elevated temperature for a period of time. The pressurized gas may be $CO_2$, $N_2O$, and $CH_4$, and the pressure may start at 1 atm, whereas under slightly elevated pressure, the reaction temperature may be lowered, while the reaction time may be shortened.

Figure 1:
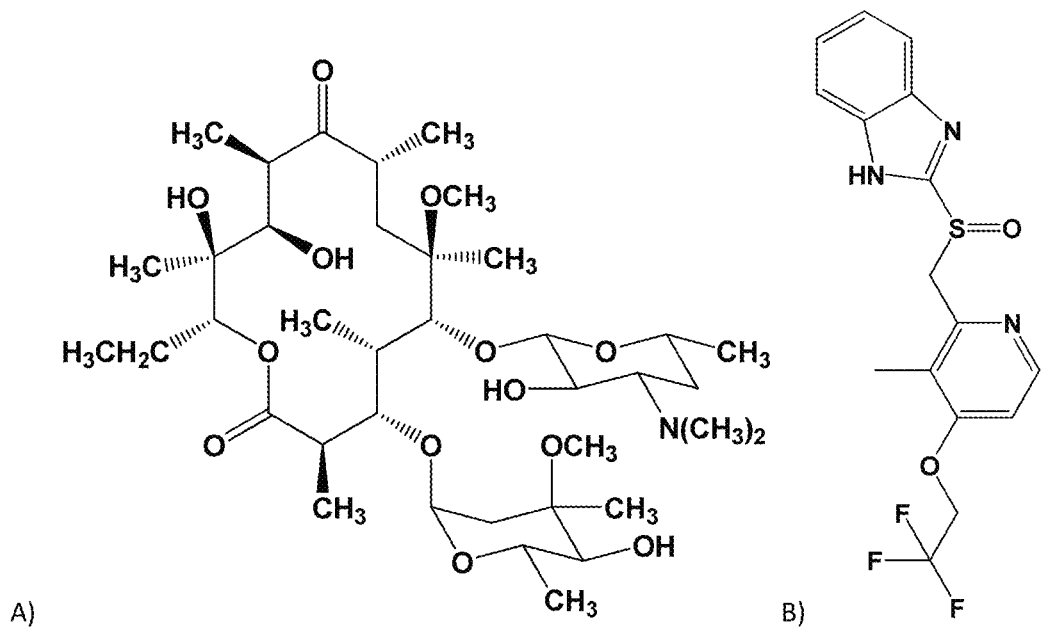
FIG. 1. Chemical structures of A) clarithromycin 1 and B) Lansoprazole 2.
Figure 2:
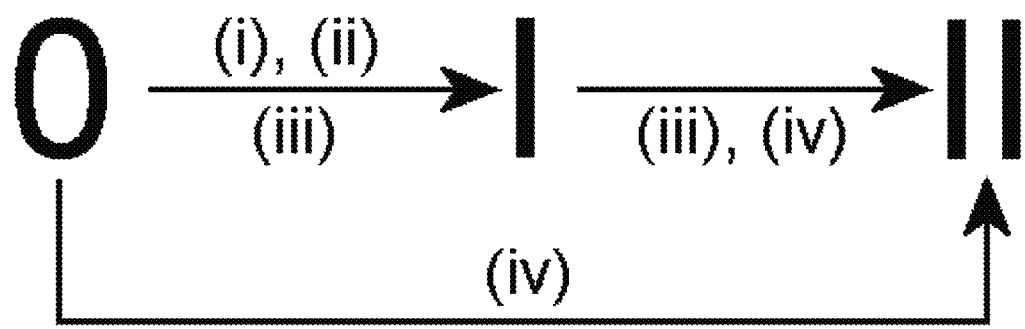
FIG. 2. Schematic of known conditions for various phase transformations of crystalline 1: (i) drying in vacuum in the temperature range of 0-50° C., (ii) exposure to air at room temperature, (iii) heating either form 0 or I in water for ~2 h. Note that these methods are performed separately and are not combined.
Figure 3:
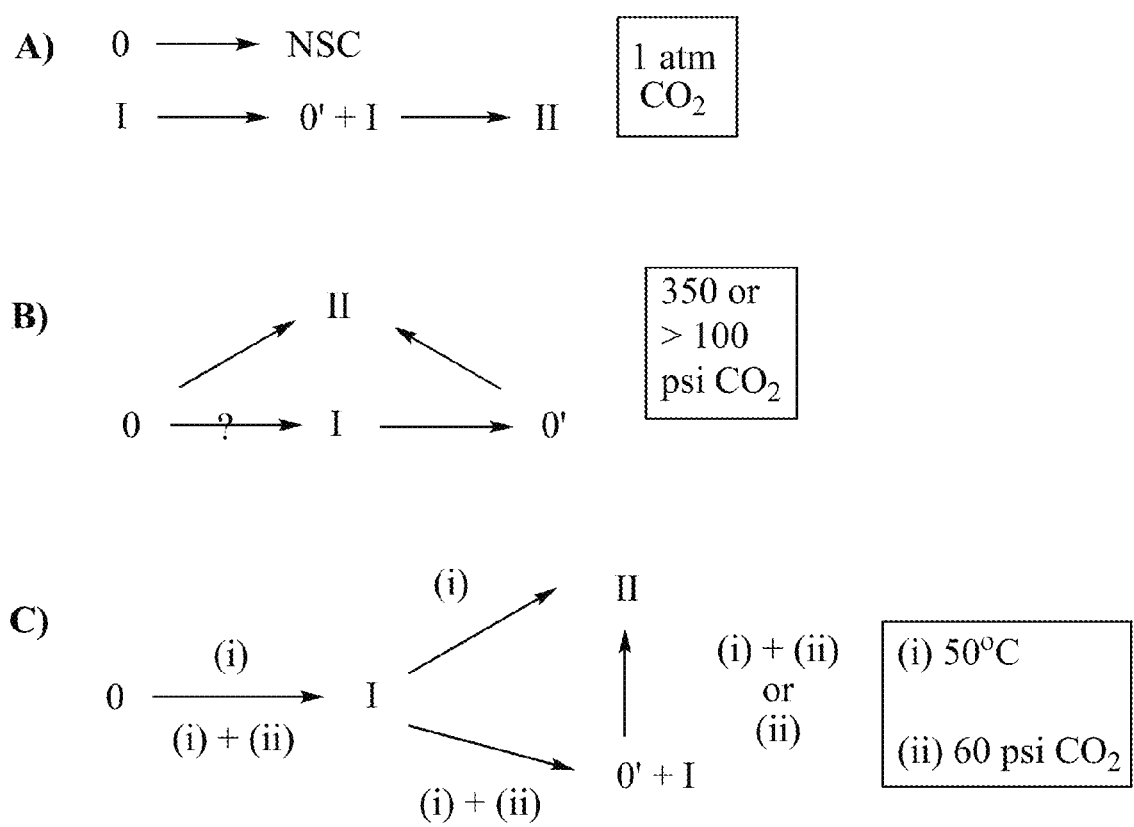
FIG. 3. Schematic illustrations of the phase transformations among different forms of Clarithromycin 1.

Refer to FIG. 3, which includes schematic illustrations of the phase transformations between different forms of Clarithromycin 1. As shown in FIG. 3, different pressure (1 to 23.8 atm) and temperature conditions have been experimented, and the inventors found that exposure of form 0 to the 23.8 atm (350 psi) $CO_2$ at room temperature for just 4 hours resulted in complete transformation directly to form II. As expected, desolvated form I can be transformed to form II with greater ease under analogous conditions. Particularly, pressurization of form I under 350 psi $CO_2$, results in transformation to form II within just several minutes. Different gases including $H_2$, He, $CH_4$, $N_2$, $O_2$, air, and $N_2O$ have been studied, among which $N_2O$ has similar transformation effect as $CO_2$.

Figure 4:
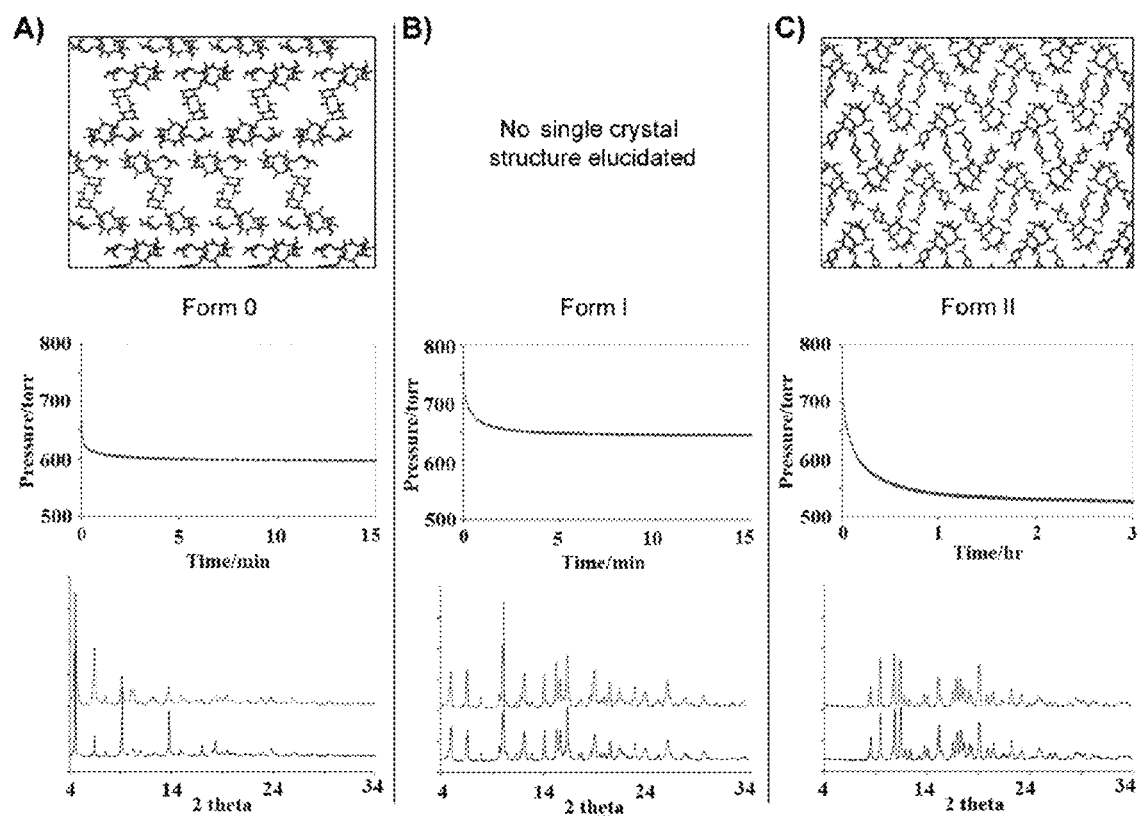
FIG. 4. Crystal structures, gas adsorption isotherms, and XRPD studies of forms 0, I, II of Clarithromycin 1.
Figure 5:
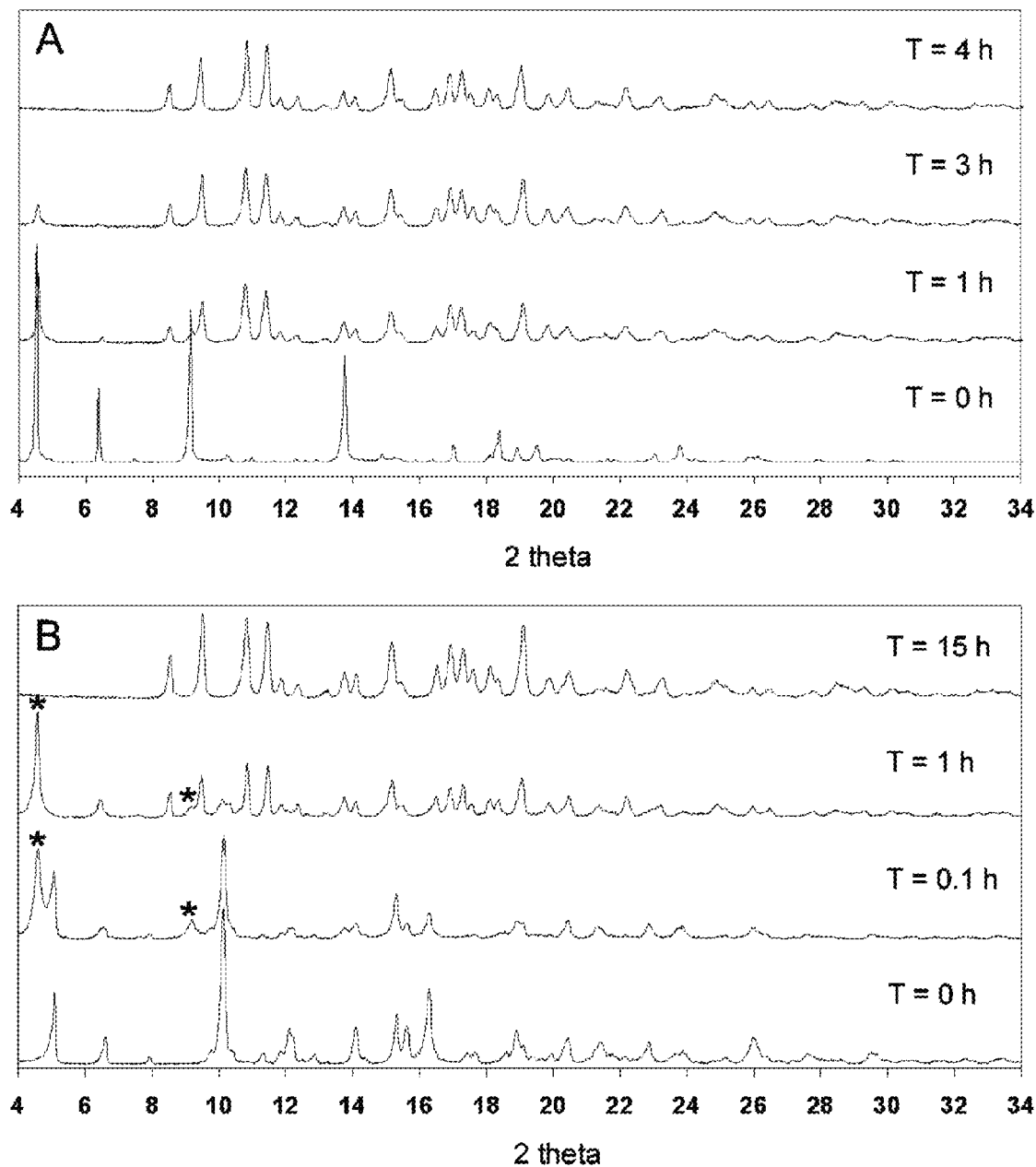
FIG. 5. X-ray powder diffraction patterns of samples of Clarithromycin 1 performed at 296K.

Refer to FIG. 4, which shows the crystal structures, gas adsorption isotherms, and XRPD studies of forms 0, I, II of Clarithromycin 1. Refer to FIG. 5, which compares the transformations under different gas pressures (350 psi vs. 100 psi) at different durations.

Figure 6:
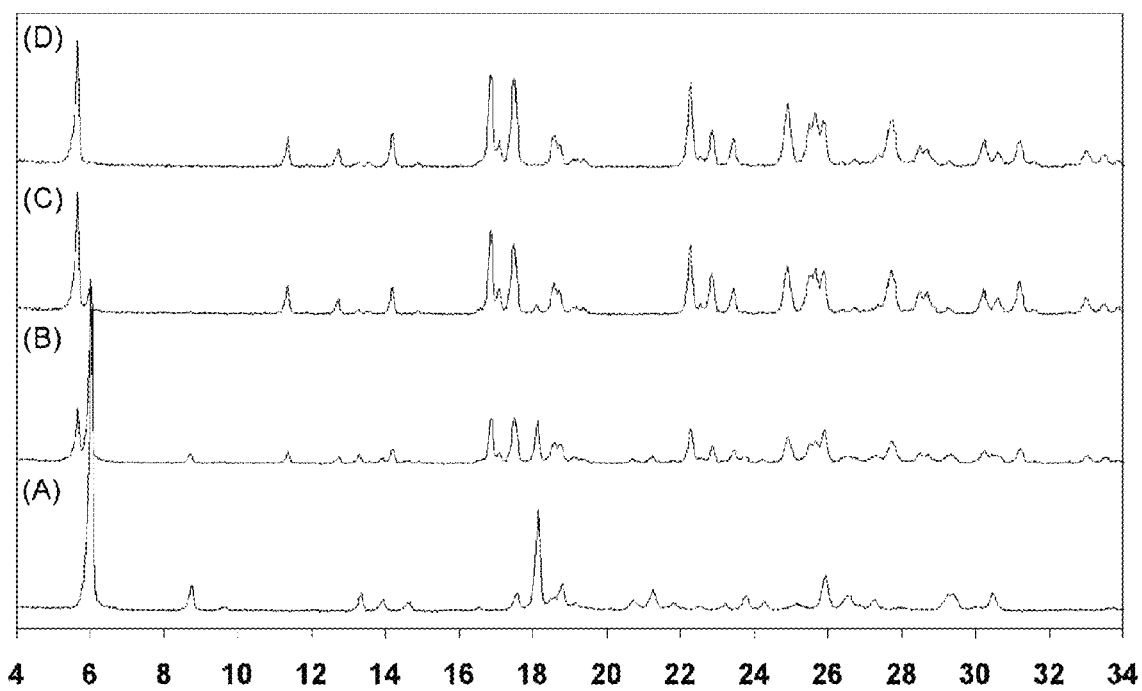
FIG. 6. X-ray powder diffraction patterns of samples of Lansoprazole 2 performed at 296K.

The invention has also studied Lansoprazole 2 transformations under CO$_2$ but at higher pressure conditions. As shown in FIG. 6, while the ethanol hydrate is pressurized with 500 psi of CO$_2$ at room temperature, the transformation to the more thermodynamically stable solvent-free form begins. Different gases have also been studied, and it has been found that N$_2$O and CH$_4$ also can affect the transformations.

More details of the invention are described in the article titled Tian, Jian, Scott J. Dalgarno, and Jerry L. Atwood. "A new strategy of transforming pharmaceutical crystal forms." *Journal of the American Chemical Society* 133.5 (2011): 1399-1404. which is incorporated hereby in its entirety.

While the invention has been described in connection with specific embodiments thereof, it will be understood that the inventive device is capable of further modifications. This patent application is intended to cover any variations, uses, or adaptations of the invention following, in general, the principles of the invention and including such departures from the present disclosure as come within known or customary practice within the art to which the invention pertains and as may be applied to the essential features herein before set forth.

REFERENCES (1) Bernstein, J. *Polymorphism in Molecular Crystals*; Clarendon, Oxford, 2002.
(2) Brittain, H. G. *Polymorphism in Pharmaceutical Solids*; Marcel Dekker, Inc.: New York, 1999.
(3) Bernstein, J.; Dunitz, J. D. *Acc. Chem. Res.* 1995, 28, 193.
(4) Davey, R. *J. Chem. Commun,* 2003, 1463.
(5) Morimoto, S.; Misawa, Y.; Adachi, T.; Nagate, T.; Watanabe, Y.; Omura, S, Y. *J. Alltibiot.* 1990, 43, 286.
(6) Piscitelli, S. C.; DanZiger, L. H.; Rodvold, K. A. *Clinn. Pharm.* 1992, 11, 137.
(7) Spanton, S. G.; Henry, R. F.; Riley, D. A.; Liu, J-H. U.S. Pat. No. 5,945,405, 1999.
(8) Liu, J-H.; Riley, D. A.; Spanton, S. G. U.S. Pat. No. 5,858,986, 1999.
(9) Liu" J-H.; Riley, D. A. Preparation of crystal form 11 of clarithromycin, U.S. Pat. No. 5,844,105, 1998.
(10) Stephenson, G. A.; Stowell, J. G.; Toma, P. H.; Pfeiffer, R. R.; Byrn, S. R. *J. Pharm. Sci.* 1997, 86, 1239.
(11) Liu, J-H; Henry, R. F.; Spanton, S. G.; Riley, D. A. U.S. Pat. No. 6,627,743, 2003.
(12) Liang, J-H; Yao, G. W. *J. Chem. Crystallogr.* 2008, 38, 61.
(13) Avrutov, L.; Lifshitz, I.; Borochovitz, R.; Masarwa, B.; Schwartz, E. U.S. Pat. No. 6,599,884, 2003.
(14) IMS National Sales Perspectives, IMS HEALTH, a health care information company, http://www.imshealth.com.
(15) Kato, M.; Ishida, T. U.S. Pat. No. 6,002,011, 1999.
(16) See, for example: (a) Brittain, H. G. J. Pharm, Sci, 2002, 91, 1573, (b) Dawson, A.; Allan, D. R.; Belmonte, S. A.; Clark, S. J.; David, W. F.; McGregor, P. A.; Parsons, S.; Pulham, C. R.; Sawyer, L. Cryst. Growth Des. 2005, 5, 1415, (c) Fabbiani, F. P. A.; Pulham, C. R. Chem. Soc. Rev. 2006, 35, 932. (d) Johnstone, R. D. L.; Ieva, M.; Lennie, A. R.; McNab, H.; Pidcock, E.; Warren, J. E.; Parsons, S. Cryst. Eng. Comm. 2010, 12, 2520.
(17) (a) Subramanian, B.; Rajewski, R. O.; Snavely, K.; Pharm. Sci. 1997, 86, 885, (b) Bettini, R.; Bonassi, L.; Castoro, V.; Rossi, A.; Zema, L.; Gazzaniga, A.; Giordano, F. Eur, J. Pharm. Sci. 2001, 13, 281. (c) Tozuka, Y.; Kawada, D.; Oguchi, T.; Yamamoto, K. Int. J. Pharm. 2003, 263, 45, (d) Moribe, K.; Tozuka, Y.; Yamamoto, K. Adv. Drug Delivery Rev. 2008, 60, 328.
(18) Thallapally, P. K.; McGrail, B. P.; Dalgarno, S. J.; Schaef, H. T.; Tian, J.; Atwood, J. L. *Nat. Mater.* 2008, 7, 146.
(19) *SAINT+*, version 6.22; Bruker Analytical X-Ray Systems, Inc.: Madison, Wis., 2001.
(20) Sheldrick, G. M. *SHELX*-97; Bruker Analytical X-Ray Systems, Inc.: Madison, Wis., 1997.
(21) Lifshitz, L.; Avrutov, L.; Schwartz, E.; Masarwa, B. U.S. Pat. No. 6,396,624 292, 2003.
(22) Jin, Z. M.; Ma, L. L.; Wei, W. X.; Lin, C. S.; Li, W. Z. J. Struct. Chem. 2009, 50, 185.
(23) Iwasaki, H.; Sugawara, Y.; Adachi, T.; Morimoto, S.; Watanabe, Y. *Acta Crysiallogr.* C 1993, C49, 1227.
(24) Tian, J.; Thallapally, P. K.; Dalgarno, S. J.; Atwood, J. L. J. Am. Chem. Soc. 2009, 131, 13216.
(25) Kato, M.; Toyoshima, Y.; Iwano, N. U.S. Pat. No. 5,578, 732, 1996.
(26) Vyas, K.; Sivalakshmidevi, A.; Om Reddy, G. *Acta Crystallogr.* C 2000, C56, e572.

What claimed is:

1. A method for transforming an organic solid from a first polymorphic form to a second polymorphic form, wherein the organic solid is clarithromycin or lansoprazole, comprising the step of subjecting clarithromycin to a pressurized gas selected from the group consisting of CO$_2$ and N$_2$O or lansoprazole to a pressurized gas selected from the group consisting of CO$_2$ N$_2$O and CH$_4$ at less than 40 atm, at a temperature under 100° C. for a period of time, wherein said combinaton of pressure and temperature is sufficient to cause a polymorphic transformation in said organic solid.

2. A method for transforming an organic solid from a mixture of polymorphic forms to a single polymorphic form, wherein the organic solid is clarithromycin or lansoprazole, comprising the step of subjecting clarithromycin to a pressurized gas selected from the group consisting of CO$_2$ and N$_2$O or lansoprazole to a pressurized gas selected from the group consisting of CO$_2$ N$_2$O and CH$_4$ at less than 40 atm, at a temperature under 100° C. for a period of time, wherein said combination of pressure and temperature is sufficient to cause a polymorphic transformation in said organic solid.

3. A method for transforming an organic solid from a solvated form to a desolvated form, wherein the organic solid is clarithromycin or lansoprazole, comprising the step of subjecting clarithromycin to a pressurized gas selected from the group consisting of CO$_2$ and N$_2$O or lansoprazole to a pressurized gas selected from the group consisting of CO$_2$, N$_2$O and CH$_4$ at less than 40 atm, at a temperature under 100° C. for a period of time, wherein said combinaton of pressure and temperature is sufficient to cause desolvation in said organic solid.

4. A method of screening an organic solid for polymorphic form, wherein the organic solid is clarithromycin or lansoprazole, comprising the step of subjecting clarithromycin to a pressurized gas selected from the group consisting of CO$_2$ and N$_2$O or lansoprazole to a ressurized gas selected from the group consisting of CO$_2$ N$_2$O and CH$_4$ at less than 40 atm, at a temperature under 100° C. for a period of time, wherein said combination of pressure and temperature is sufficient to cause a polymorphic transformation in said organic solid.

5. The method of any of claim 1, 2, 3, or 4, wherein said organic solid is subjected to a pressurized gas at less than 10 atm.

6. The method of claim 5, wherein said organic solid is subjected to a pressurized gas at less than 5 atm.

7. The method of any of claims 1, 2, 3 or 4, wherein said organic solid is subjected to temperature under 50° C.

8. The method of any of claims 1, 2, 3, or 4, wherein said organic solid is clarithromycin.

9. The method of any of claims 1, 2, 3 or 4, wherein said organic solid is lansoprazole.

* * * * *